(12) United States Patent
Kakehashi

(10) Patent No.: US 9,872,608 B2
(45) Date of Patent: Jan. 23, 2018

(54) BENDING DEVICE AND ENDOSCOPE

(71) Applicant: OLYMPUS CORPORATION, Tokyo (JP)

(72) Inventor: Taigo Kakehashi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/266,471

(22) Filed: Sep. 15, 2016

(65) Prior Publication Data

US 2017/0000312 A1 Jan. 5, 2017

Related U.S. Application Data

(63) Continuation of application No. PCT/JP2015/065748, filed on Jun. 1, 2015.

(30) Foreign Application Priority Data

Jun. 18, 2014 (JP) .................. 2014-125636

(51) Int. Cl.
*A61B 1/00* (2006.01)
*A61B 1/005* (2006.01)
(Continued)

(52) U.S. Cl.
CPC ............ *A61B 1/0055* (2013.01); *A61B 1/005* (2013.01); *A61B 1/0051* (2013.01);
(Continued)

(58) Field of Classification Search
CPC ..... A61B 1/005; A61B 1/0051; A61B 1/0052; A61B 1/0053; A61B 1/0055; A61B 1/0056; A61B 1/0057; A61B 1/0058; A61B 1/008; A61B 1/00071; A61B 1/00078; A61B 2017/003; A61B 2017/00318; A61B 2017/00331; A61B 2017/00305; A61B 2017/00309; A61B 2017/00314; A61B 2017/00323; A61B 2017/00327; A61B 1/01; A61B 2034/301; A61M 25/0102; A61M 25/0133; A61M 25/0136; A61M 25/0138; A61M 25/0141; A61M 25/0144; A61M 25/0147; A61M 2025/015; A61M 2025/0161
(Continued)

(56) References Cited

U.S. PATENT DOCUMENTS

2013/0112457 A1  5/2013 Kitagawa

FOREIGN PATENT DOCUMENTS

JP   H02-261418 A   10/1990
JP   H09-294711 A   11/1997
(Continued)

OTHER PUBLICATIONS

International Search Report dated Aug. 25, 2015 issued in PCT/JP2015/065748.
(Continued)

*Primary Examiner* — Ryan Henderson
(74) *Attorney, Agent, or Firm* — Scully, Scott, Murphy & Presser, P.C.

(57) ABSTRACT

A bending device includes a bending section, a wire, a wire receiver, a cover, a fixed section against which a distal end of the cover is buttable when the cover advances and retracts, and a coil sheath against which a proximal end of the cover is buttable when the cover advances and retracts.

7 Claims, 7 Drawing Sheets

(51) Int. Cl.
*A61M 25/01* (2006.01)
*A61B 17/00* (2006.01)

(52) U.S. Cl.
CPC ....... *A61B 1/0057* (2013.01); *A61M 25/0133* (2013.01); *A61M 25/0138* (2013.01); *A61M 25/0141* (2013.01); *A61M 25/0144* (2013.01); *A61M 25/0147* (2013.01); *A61B 2017/003* (2013.01); *A61B 2017/00314* (2013.01); *A61B 2017/00318* (2013.01); *A61B 2017/00323* (2013.01); *A61B 2017/00327* (2013.01)

(58) Field of Classification Search
USPC .................................................. 600/139–152
See application file for complete search history.

(56) References Cited

FOREIGN PATENT DOCUMENTS

| JP | H10-005172 A | 1/1998 |
| JP | H10-328130 A | 12/1998 |
| JP | 2005-237608 A | 9/2005 |
| JP | 2009-78012 A | 4/2009 |
| JP | 2012-040308 A | 3/2012 |
| WO | WO 2011-092937 A1 | 8/2011 |
| WO | WO 2012/026231 A1 | 3/2012 |

OTHER PUBLICATIONS

Japanese Office Action dated Mar. 1, 2016 issued in JP 2015-557672.

BENDING DEVICE AND ENDOSCOPE

CROSS REFERENCE TO RELATED APPLICATION

This application is a continuation application of PCT/JP2015/065748 filed on Jun. 1, 2015 and claims benefit of Japanese Application No. 2014-125636 filed in Japan on Jun. 18, 2014, the entire contents of which are incorporated herein by this reference.

BACKGROUND OF THE INVENTION

1. Field of the Invention

The present invention relates to a bending device that bends a bending section by towing of a wire and to an endoscope.

2. Description of the Related Art

In recent years, a medical instrument inserted into a subject, for example, an endoscope, has been widely used in a medical field. The endoscope can perform observation, treatment, and the like of a region to be examined in the subject by inserting an elongated insertion section into the subject.

A configuration is well-known in which a bending section bendable in a plurality of directions configuring a bending device is provided in the insertion section of the endoscope.

The bending section improves progression of the insertion section in a bent section in a conduit and changes, in the insertion section, an observation direction of an observation optical system provided in a distal end portion concatenated to a distal end in a longitudinal axis direction (hereinafter simply referred to as distal end) of the insertion section in the bending section.

Usually, a plurality of bending pieces are coupled by rivets or the like along the longitudinal axis direction of the insertion section, whereby the bending section is configured to be bendable in, for example, upward, downward, left, and right four directions.

More specifically, any one of four wires inserted to be movable to a front and a back in the longitudinal axis direction (hereinafter simply referred to as the front and the back) in the insertion section and configuring a bending device, a distal end of which fixed to the bending piece located on a most distal end side in the longitudinal axis direction (hereinafter simply referred to as distal end side) among the plurality of bending pieces, is towed using a bending operation knob of an operation section, whereby the bending section is bendable in any one of the upward, downward, left, and right directions. Note that the four wires are inserted while being shifted, in the bending piece, from one another in a circumferential direction of the bending piece by approximately 90° along an inner circumferential surface of the bending piece.

On inner circumferential surfaces of the plurality of bending pieces, the four wires are inserted along the longitudinal axis direction, whereby wire receivers configuring the bending device that hold the respective wires to be advanceable and retractable in the longitudinal axis direction along the inner circumferential surfaces of the plurality of bending pieces are provided while being shifted from one another in the circumferential direction by approximately 90° for each of the wires. The respective wire receivers hold the respective wires such that the respective wires do not shift in the circumferential direction and a radial direction of the bending pieces.

A configuration is also well-known in which the bending section provided in the insertion section of the endoscope is configured from a first bending section and a second bending section concatenated to a proximal end in the longitudinal axis direction (hereinafter simply referred to as proximal end) of the first bending section.

In such a configuration, the respective distal ends of the four wires are fixed to a distal end of the first bending section. In the second bending section, coil sheathes, distal ends of which are fixed to a distal end of the second bending section and proximal ends of which are switchable to a fixed state and an unfixed state, are respectively covered on outer circumferential of the respective wires.

If the proximal ends of the respective coil sheathes are fixed, when any one of the four wires is towed, the respective coil sheathes resist a compression force applied in the longitudinal axis direction. Therefore, only the first bending section is bent. If the proximal ends of the respective coil sheathes are not fixed, when any one of the four wires is towed, the second bending section bends in the same direction with the first bending section.

Note that, in the second bending section, coil sheathes formed by densely winding four element wires are inserted through the respective wire receivers along the longitudinal axis direction.

Consequently, the respective wire receivers hold the respective coil sheathes to be advanceable and retractable in the longitudinal axis direction along the inner circumferential surfaces of the plurality of bending pieces. More specifically, the respective wire receivers hold the respective wires such that the respective coil sheathes do not shift in the circumferential direction and the radial direction of the bending pieces.

When the bending section is bent, when any one of the four wires is towed, the towed wire is pressed against the inner circumferential surfaces of the plurality of bending pieces that bend in one direction.

This is the same when the coil sheathes are provided in the insertion section. When the second bending section is bent with the first bending section, the coil sheathes are pressed against the inner circumferential surfaces of the plurality of bending pieces configuring the second bending section that bends in one direction.

As a result, the wires and the coil sheathes are pressed against the respective wire receivers located while having a set interval along the longitudinal axis direction. Large forces are locally generated in contact places of the wires and the coil sheathes with the respective wire receivers. That is, large sliding resistance is locally generated.

Therefore, a problem arises that a force amount for towing the wires increases, that is, not only an operation force amount of the wires increases but also the wires and the coil sheathes are easily worn.

In view of such a problem, Japanese Patent Application Laid-Open Publication No. 2009-78012 discloses a configuration in which coil springs including sparsely wound regions and densely wound regions are respectively covered on outer circumferences of respective wires inserted through a bending section respectively, whereby, when the wires are towed, the wires are prevented by the coils springs from being directly pressed against wire receivers.

Note that, since the coil springs can also be covered on the outer circumferences of the coil sheathes, in the configuration in which the bending sections include the first bending section and the second bending section, if the coil springs are used, it is also possible to prevent, with the coil springs, the coil sheaths from being directly pressed against the wire receivers.

SUMMARY OF THE INVENTION

A bending device according to an aspect of the present invention includes: a bendable bending section; a wire, a distal end of which is fixed to the bending section, the wire being towed to bend the bending section; a plurality of wire receivers provided on an inner circumferential surface of the bending section, the wire being inserted through the wire receivers in an advanceable and retractable manner; a cover that covers all regions held by the plurality of wire receivers in an outer circumference of the wire, is inserted through the wire receivers with the wire, has stretchability in a longitudinal axis direction of the wire, and is advanceable and retractable in the longitudinal axis direction in the bending section; a fixed section against which a distal end of the cover is buttable when the cover advances and retracts; and a coil sheath against which a proximal end of the cover is buttable when the cover advances and retracts.

A bending device according to another aspect of the present invention includes: a bendable bending section in which a plurality of bending pieces are coupled; a wire, a distal end of which is fixed to the bending section, the wire being towed to bend the bending section; a plurality of wire receivers provided on an inner circumferential surface of the bending section, the wire being inserted through the wire receivers in an advanceable and retractable manner; an inner coil sheath, a distal end of which is fixed to a cap interposed between the bending pieces in an intermediate section of the bending section, the inner coil sheath being inserted through the plurality of wire receivers further on a proximal end side than the cap and extended to the proximal end side of the bending section; a cover that covers all regions held by the plurality of wire receivers on the proximal end side from the cap in an outer circumference of the inner coil sheath, is inserted through the wire receivers with the wire, has stretchability in a longitudinal axis direction of the wire, and is advanceable and retractable in the longitudinal axis direction in the bending section further on the proximal end side than the cap; a fixed section at a distal end of the inner coil sheath against which a distal end of the cover is buttable when the cover advances and retracts; and an outer coil sheath against which a proximal end of the cover is buttable when the cover advances and retracts, and through an inner side which, the inner coil sheath is inserted.

An endoscope according to an aspect of the present invention includes the bending device according to the aspect described above.

An endoscope according to another aspect of the present invention includes the bending device according to the other aspect described above.

DETAILED DESCRIPTION OF THE PREFERRED EMBODIMENT(S)

Embodiments of the present invention are described below with reference to the drawings. Note that the drawings are schematic and relations between thicknesses and widths of respective members, ratios of the thicknesses of the respective members, and the like are different from real ones. It goes without saying that portions, relations and ratios of dimensions of which are different from one another, are included among the drawings. Note that, in the following explanation, a bending device provided in an endoscope is described as an example.

(First Embodiment)

Figure 1:
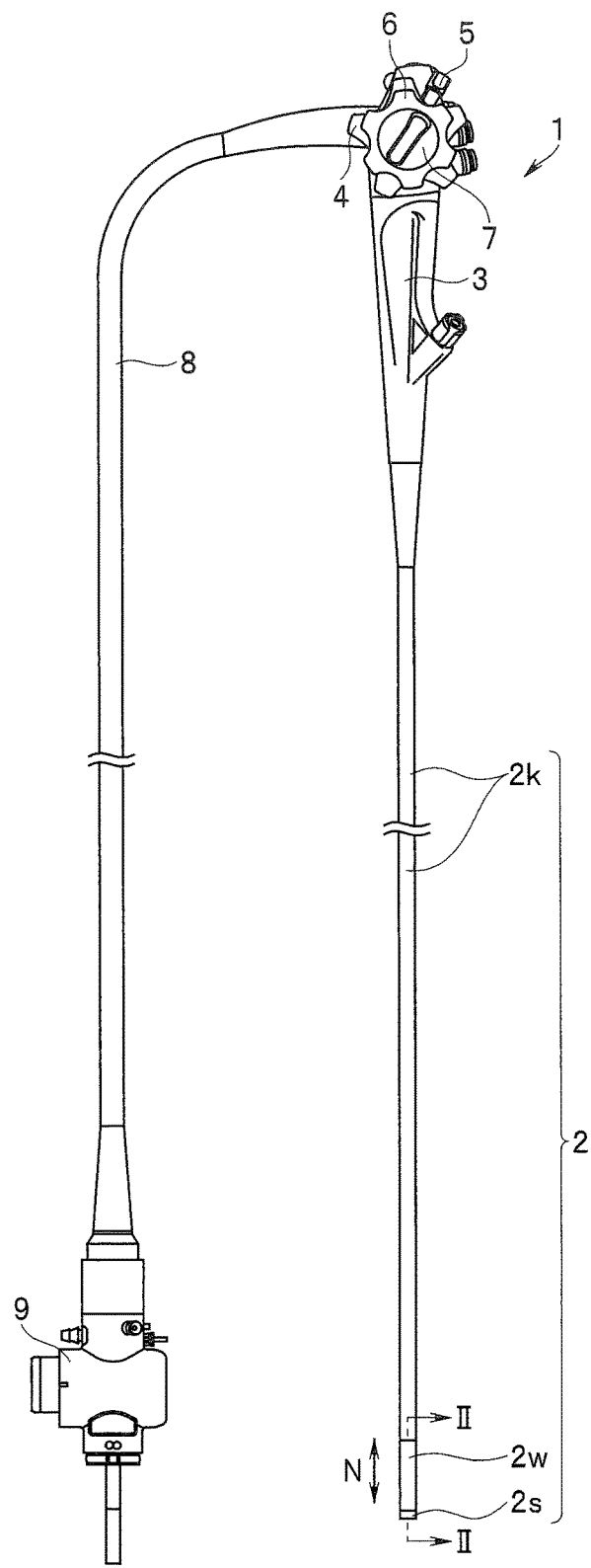
FIG. 1 is a diagram showing an exterior of an endoscope including a bending device in a first embodiment.

FIG. 1 is a diagram showing an exterior of an endoscope including a bending device in the present embodiment.

As shown in FIG. 1, a main part of an endoscope 1 is configured by including an insertion section 2 inserted into a subject, an operation section 3 concatenated to a proximal end of the insertion section 2, a universal cord 8 extended from the operation section 3, and a connector 9 provided at an extension end of the universal cord 8. Note that the endoscope 1 is electrically connected to an external apparatus such as a control apparatus or an illumination apparatus via the connector 9.

A main part of the insertion section 2 is configured by including a long flexible tube 2k having flexibility extending along a longitudinal axis direction N of the insertion section 2, a bending section 2w configuring a bending device concatenated to a distal end of the flexible tube 2k, and a distal end portion 2s concatenated to a distal end of the bending section 2w.

In the distal end portion 2s, a not-shown image pickup unit that picks up an image in a subject, a not-shown illumination unit that supplies illumination light into the subject, and the like are provided.

The bending section 2w is bendable in, for example, upward, downward, left, and right four directions by bending operation knobs 4 and 6 described below provided in the operation section 3.

More specifically, in the operation section 3, the bending operation knob 4 that bends the bending section 2w in an up-down direction and the bending operation knob 6 that bends the bending section 2w in a left-right direction are provided.

In the operation section 3, a not-shown pulley for up-down bending that turns with the bending operation knob 4 to thereby tow and slack wires 10u and 10d (see FIG. 3) described below inserted through the insertion section 2 and the operation section 3 to thereby bend the bending section 2w in the up-down direction is provided.

Further, in the operation section 3, a pulley for left-right bending that turns with the bending operation knob 6 to thereby tow and slack wires 10r and 10l (see FIG. 3) described below inserted through the insertion section 2 and the operation section 3 to thereby bend the bending section 2w in the left-right direction is provided.

Note that, since the pulley for up-down bending and the pulley for left-right bending are well known, detailed explanation using the drawings is omitted.

In the operation section 3, a fixing lever 5 that fixes a turning position of the bending operation knob 4 is provided and a fixing knob 7 that fixes a turning position of the bending operation knob 6 is provided.

A configuration of a main part related to the present embodiment on a distal end side of the insertion section shown in FIG. 1 is described with reference to FIG. 2 and FIG. 3.

Figure 2:
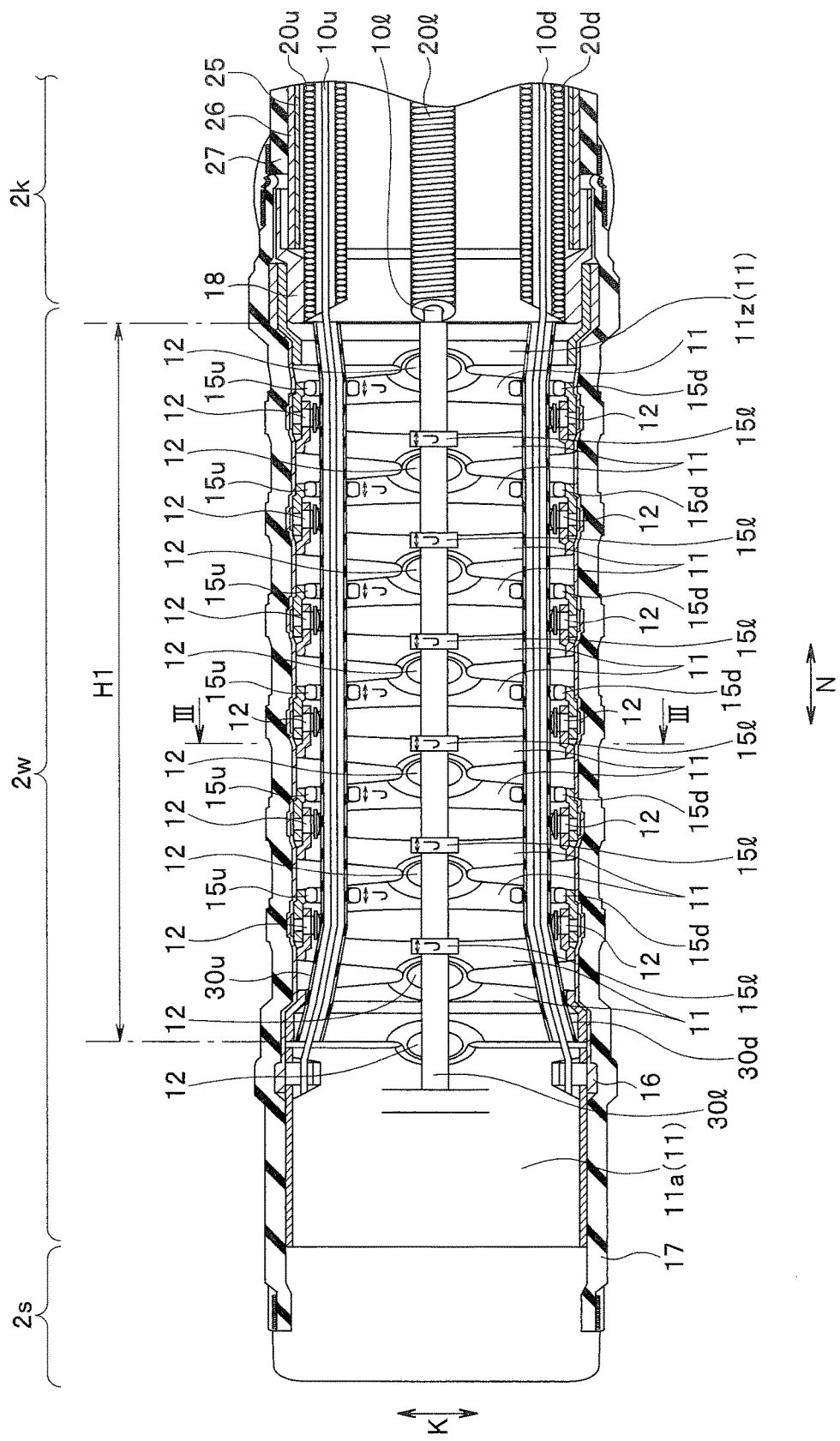
FIG. 2 is a partial sectional view of an insertion section taken along line II-II in FIG. 1.

FIG. 2 is a partial sectional view of the insertion section taken along line II-II in FIG. 1. FIG. 3 is a sectional view of the bending section taken along line in FIG. 2.

As shown in FIG. 2, on an inside of the bending section 2w, a plurality of cylindrical bending pieces 11 are coupled and provided along the longitudinal axis direction N.

Note that the plurality of bending pieces 11 are turnably coupled to the pieces adjacent to one another in the longitudinal axis direction N by a plurality of rivets 12 to be bendable in the upward, downward, left, and right four directions.

A braid 16 is covered on outer circumference of the plurality of bending pieces 11. Bending rubber 17 is covered on an outer circumference of the braid 16.

Figure 3:
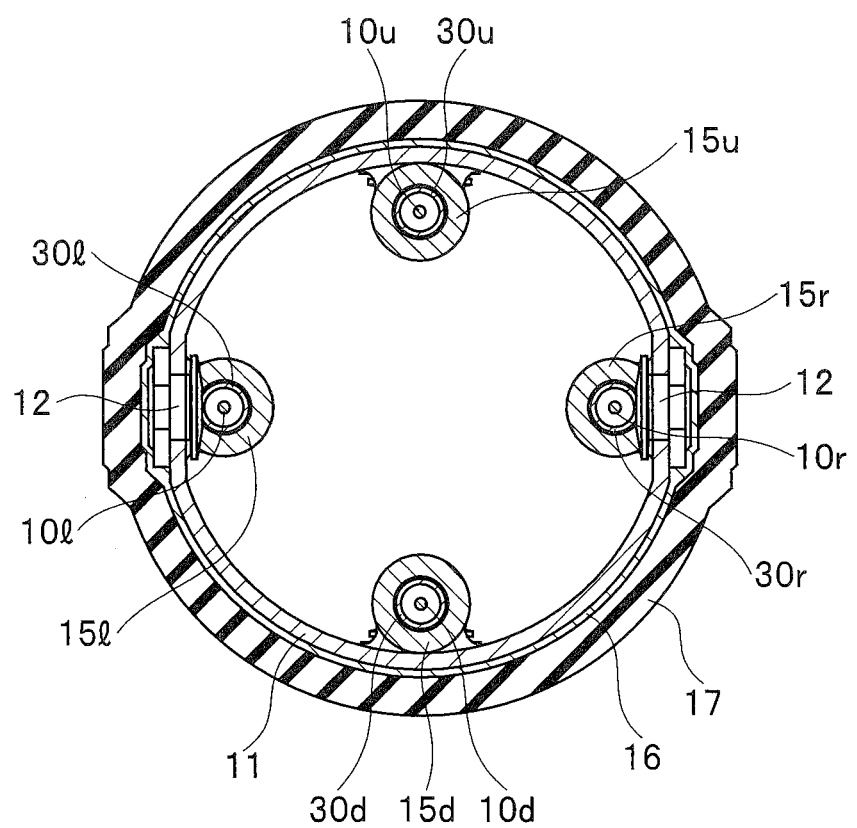
FIG. 3 is a sectional view of a bending section taken along line in FIG. 2.

As shown in FIG. 2 and FIG. 3, in the insertion section 2 and the operation section 3, the wires 10r, 10l, 10u, and 10d configuring, for example, four bending devices, which bend the bending section 2w according to towing and are advanceable and retractable to a front and a back, are inserted through while being shifted from one another in a circumferential direction of the insertion section 2 by approximately 90°.

Distal ends of the respective wires 10r to 10d are fixed to a bending piece 11a located on a most distal end side among the plurality of bending pieces 11 provided in the bending section 2w.

Pluralities of tubular wire receivers 15r, 15l, 15u, and 15d configuring the bending devices that hold the wires 10r to 10d to be advanceable and retractable in the longitudinal axis direction N such that the wires 10r to 10d are inserted through along the longitudinal axis direction and the wires 10r to 10d are located along inner circumferential surfaces of the respective bending pieces 11 and while being shifted from one another in the circumferential direction by approximately 90° are fixed on the inner circumferential surfaces of the respective bending pieces 11 while having a set interval in the longitudinal axis direction N.

More specifically, the wire receivers 15r to 15d are also fixed while being shifted in the circumferential direction by approximately 90°. The wire 10r is inserted through the plurality of wire receivers 15r provided while having the set interval in the longitudinal axis direction N. The wire 10l is inserted through the plurality of wire receivers 15l provided while having the set interval in the longitudinal axis direction N. Further, the wire 10u is inserted through the plurality of wire receivers 15u provided while having the set interval in the longitudinal axis direction N. The wire 10d is inserted through the plurality of wire receivers 15d provided while having the set interval in the longitudinal axis direction N.

Note that respective proximal ends of the two wires 10u and 10d for up-down bending are wound on the pulley for up-down bending described above. Respective proximal ends of the two wires 10r and 10l for left-right bending are wound on the pulley for left-right bending described above.

That is, when the bending operation knob 4 is operated, one of the two wires 10u and 10d for up-down bending is moved backward in the longitudinal axis direction N and the other is moved forward in the longitudinal axis direction N by the pulley for up-down bending. Consequently, one is towed and the other is slacked, whereby the bending section 2w bends in the upward or downward direction.

When the bending operation knob 6 is operated, one of the two wires 10r and 10l for left-right bending is moved backward in the longitudinal axis direction N and the other is moved forward in the longitudinal axis direction N by the pulley for left-right bending. Consequently, one is towed and the other is slacked, whereby the bending section 2w bends in the left or right direction.

A distal end side of a coupling member 18 is fixed to an inner circumference of a bending piece 11z located on a most proximal end side in the longitudinal axis direction N (hereinafter simply referred to as proximal end side) among the bending pieces 11. A distal end side of a braid configuring the flexible tube 2k is fixed to an inner circumference on a proximal end side of the coupling member 18.

Note that the braid is configured from, for example, a spiral tube 25 made of metal and a mesh tube 26 covered on an outer circumference of the spiral tube 25. An outer coat tube 27 is covered on an outer circumference of the mesh tube 26.

For example, coil sheathes 20r, 20l, 20u, and 20d (the coil sheath 20r is not shown in the figure) flexible and elongated along the longitudinal axis direction N are respectively covered on outer circumferences of the respective four wires 10r to 10d inserted through the flexible tube 2k.

That is, in the flexible tube 2k, the respective four coil sheathes 20r to 20d are inserted through in positions shifted from one another in a circumferential direction of the flexible tube 2k by approximately 90°.

Distal ends of the respective coil sheathes 20r to 20d are fixed to the distal end of the flexible tube 2k, more specifically, the coupling member 18 by, for example, brazing. Further, proximal ends of the respective coil sheathes 20r to 20d are fixed in the operation section 3.

The respective coil sheathes 20r to 20d guide the respective wires 10r to 10d to be movable along the longitudinal axis direction N without shifting in a radial direction K and the circumferential direction of the flexible tube 2k. Further, the respective coil sheathes 20r to 20d have a function of, when the bending section 2w is bent according to towing of any one of the respective wires 10r to 10d, because distal ends and proximal ends are fixed, being compressed in the longitudinal axis direction N and resisting force of the compression to thereby prevent even the flexible tube 2k from bending with the bending section 2w.

Note that the coil sheathes 20r to 20d are formed of, for example, coil pipes of stainless steel, which is a flexible material.

The respective coil sheathes 20r to 20d are configured from flexible densely wound coils because, for example, if hard pipes made of metal are covered on outer circumferences of the respective wires 10r to 10d, flexibility of the flexible tube 2k is deteriorated.

Therefore, members configuring the respective coil sheathes 20r to 20d are not limited to coils as long as the members do not deteriorate the flexibility of the flexible tube 2k and, in the bending of the bending section 2w, can resist the compressing force acting in the longitudinal axis direction N of the respective coil sheathes 20r to 20d.

As shown in FIG. 2 and FIG. 3, in the bending section 2w, covers 30r, 30l, 30u, and 30d having stretchability with a constant stretching ratio are provided over an entire length in the longitudinal axis direction N.

The covers 30r, 30l, 30u, and 30d are covered on all regions J at least held by the respective wire receivers 15r to 15d in the outer circumferences of the respective wires 10r to 10d. The covers 30r, 30l, 30u, and 30d are inserted through the respective wire receivers 15r to 15d with the respective wires 10r to 10d and are formed to be advanceable and retractable in the longitudinal axis direction N with respect to the respective wire receivers 15r to 15d according to towing of any one of the wires 10r to 10d.

The respective covers 30r to 30d, regardless of the covers advancing/retracting with respect to the respective wire receivers 15r to 15d after the compression in the longitudinal axis direction N of the covers 30r to 30d involved in the bending of the bending section 2w, are formed in a length in the longitudinal axis direction N for covering all the regions J held by the respective wire receivers 15r to 15d.

Note that the respective covers 30r to 30d are further desirably not only formed to advance and retract with respect to the respective rivets 12 after the compression in the longitudinal axis direction N of the respective covers 30r to 30d involved in the bending of the bending section 2w but also formed in a length in the longitudinal axis direction N for covering the respective rivets 12.

Therefore, as the length in the longitudinal axis direction N of the respective covers 30r to 30d satisfying the covering conditions described above, in the present embodiment, length H1 for covering the outer circumferences of the respective wires 10r to 10d from the distal end to a proximal end of the bending section 2w in the longitudinal axis direction N is shown.

The respective covers 30r to 30d are configured from members having stretchability in the longitudinal axis direction N, for example, sparsely wound coils or tubes. Note that the sparsely wound coils indicate coils in which element wires configuring the coils are not in contact with one another.

The respective covers 30r to 30d are configured from the members having stretchability in the longitudinal axis direction N in order to absorb, when the bending section 2w is bent, with expansion and contraction, a route length change of any one of the respective wires 10r to 10d. Besides, the respective covers 30r to 30d are configured from the members having stretchability in the longitudinal axis direction N because, since the respective covers 30r to 30d are provided in the bending section 2w, if the respective covers 30r to 30d do not have stretchability, the bending section 2w does not bend even if any one of the respective wires 10r to 10d is towed.

Distal ends of the respective covers 30r to 30d are butted against fixed sections at the distal ends of the respective wires 10r to 10d with respect to the bending piece 11a. Proximal ends of the respective covers 30r to 30d are butted against the distal ends of the respective coil sheaths 20r to 20d.

Note that the distal ends and the proximal ends of the respective covers 30r to 30d are in an unfixed state. Consequently, the respective covers 30r to 30d are advanceable and retractable in the bending section 2w.

In this way, in the present embodiment, in the bending section 2w, the respective covers 30r to 30d, which have stretchability with the constant stretching ratio over the entire length in the longitudinal axis direction N, are covered on the outer circumferences of the respective wires 10r to 10d by the length H1 from the distal end to the proximal end of the bending section 2w.

Consequently, in the bending section 2w, the respective wires 10r to 10d are always in contact with the respective covers 30r to 30d, which have the constant stretching ratio over the entire length in the longitudinal axis direction N, over the entire length in the longitudinal axis direction N of the bending section 2w.

Therefore, even if any one of the respective wires 10r to 10d is towed and the bending section 2w bends, it is possible to prevent a situation in which any one of the respective wires 10r to 10d after the towing comes into direct contact with the respective wire receivers 15r to 15d and the respective rivets 12 and a large force is locally applied to any one of the respective wires 1 Or to 10d after the towing from the respective wire receivers 15r to 15d and the respective rivets 12.

When any one of the respective wires 10r to 10d is towed, any one of the respective covers 30r to 30d covered on the outer circumferences of the towed wires is compressed. At this point, since the stretching ratio is constant over the entire length, the cover is uniformly compressed over the entire length. Therefore, an operation force amount of any one of the respective wires 10r to 10d for compressing any one of the respective covers 30r to 30d, that is, bending the bending section 2w does not increase.

Therefore, it is possible to prevent wear of the respective wires 10r to 10d involved in the contact of the respective wires 10r to 10d with the respective wire receivers 15r to 15d and the respective rivets 12. It is possible to improve durability. Further, it is possible to prevent an operation force amount in towing of the respective wires 10r to 10d from increasing.

When the respective covers 30r to 30d are configured of sparsely wound coils, compared with when the respective covers 30r to 30d are configured from densely wound coils as in the past, the number of times the element wires configuring the respective covers 30r to 30d come into contact with the respective wire receivers 15r to 15d and the respective rivets 12 when the respective covers 30r to 30d advance and retract decreases. Therefore, it is possible to reduce frictional resistance generated among the respective wire receivers 15r to 15d, the respective rivets 12, and the respective covers 30r to 30d.

Consequently, it is possible to provide the bending device including a configuration for preventing, when the bending section 2w is bent by towing of the respective wires 1 Or to 10d, an operation force amount of the respective wires 10r to 10d from increasing while securing durability of the respective wires 10r to 10d.

(Second Embodiment)

Figure 4:
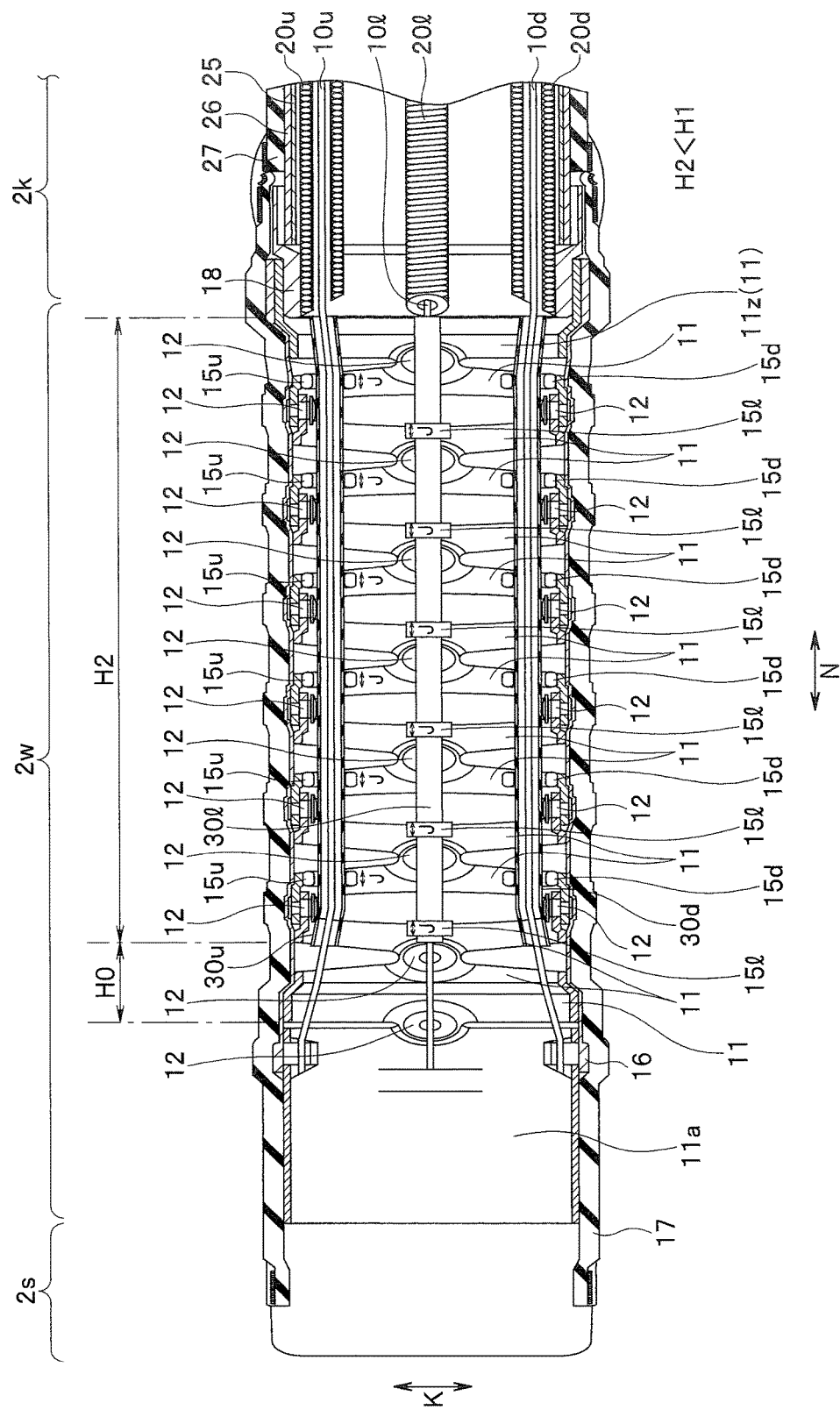
FIG. 4 is a partial sectional view of an insertion section of an endoscope including a bending device in a second embodiment.

FIG. 4 is a partial sectional view of an insertion section of an endoscope including a bending device in the present embodiment.

A configuration of the bending device in the second embodiment is different from the bending device in the first embodiment shown in FIG. 1 to FIG. 3 in that a range in which covers are provided in a bending section is different. Therefore, only the difference is described. Components same as the components in the first embodiment are denoted by the same reference numerals and signs and explanation of the components is omitted.

As shown in FIG. 4, in the present embodiment, the respective covers 30r to 30d (the cover 30r is not shown in the figure) are covered on the outer circumferences of the respective wires 10r to 10d in the bending section 2w while having length of H2 (H2<H1) in the longitudinal axis direction N such that the distal ends of the respective covers 30r to 30d are located behind the distal end of the respective wires 10r to 10d in the longitudinal axis direction N by a set interval H0 and the proximal ends of the respective covers 30r to 30d are located to the proximal end of the bending section 2w as in the first embodiment described above.

Note that, in the present embodiment, as in the first embodiment, the respective covers 30r to 30d are covered on all the regions J held by at least the respective wire receivers 15r to 15d in the outer circumferences of the respective wires 10r to 10d in the bending section 2w and are inserted through the respective wire receivers 15r to 15d with the respective wires 10r to 10d.

The respective covers 30r to 30d are formed to be advanceable and retractable in the longitudinal axis direction N with respect to the respective wire receivers 15r to 15d according to towing of any one of the wires 10r to 10d. The respective covers 30r to 30d, regardless of the covers advancing/retracting after compression with respect to the respective wire receivers 15r to 15d in the longitudinal axis direction N of the covers 30r to 30d involved in the bending of the bending section 2w, are formed in the length H2 in the longitudinal axis direction N for covering all the regions J held by the respective wire receivers 15r to 15d.

Note that the respective covers 30r to 30d, regardless of the covers advancing/retracting after compression with respect to the respective rivets 12 in the longitudinal axis direction N of the respective covers 30r to 30d involved in the bending of the bending section 2w, are further desirably formed in a length in the longitudinal axis direction N for covering the respective rivets 12.

Therefore, the respective covers 30r to 30d satisfy covering conditions same as the covering conditions in the first embodiment in the length H2 smaller than the length H1 in the first embodiment by the set interval H0.

Note that the other components are the same as the components in the first embodiment.

With such a configuration, when any one of the respective wires 10r to 10d is towed to bend the bending section 2w, a compression amount of any one of the respective covers 30r to 30d covered on the outer circumference of the towed wire is smaller than the compression amount in the first embodiment. Therefore, an operation force amount of any one of the respective wires 10r to 10d for compressing any one of the respective covers 30r to 30d is small. That is, it is possible to set the operation force amount smaller than the operation force amount in the first embodiment and bend the bending section 2w.

Note that the other effects are the same as the effects in the first embodiment.

(Third Embodiment)

Figure 5:
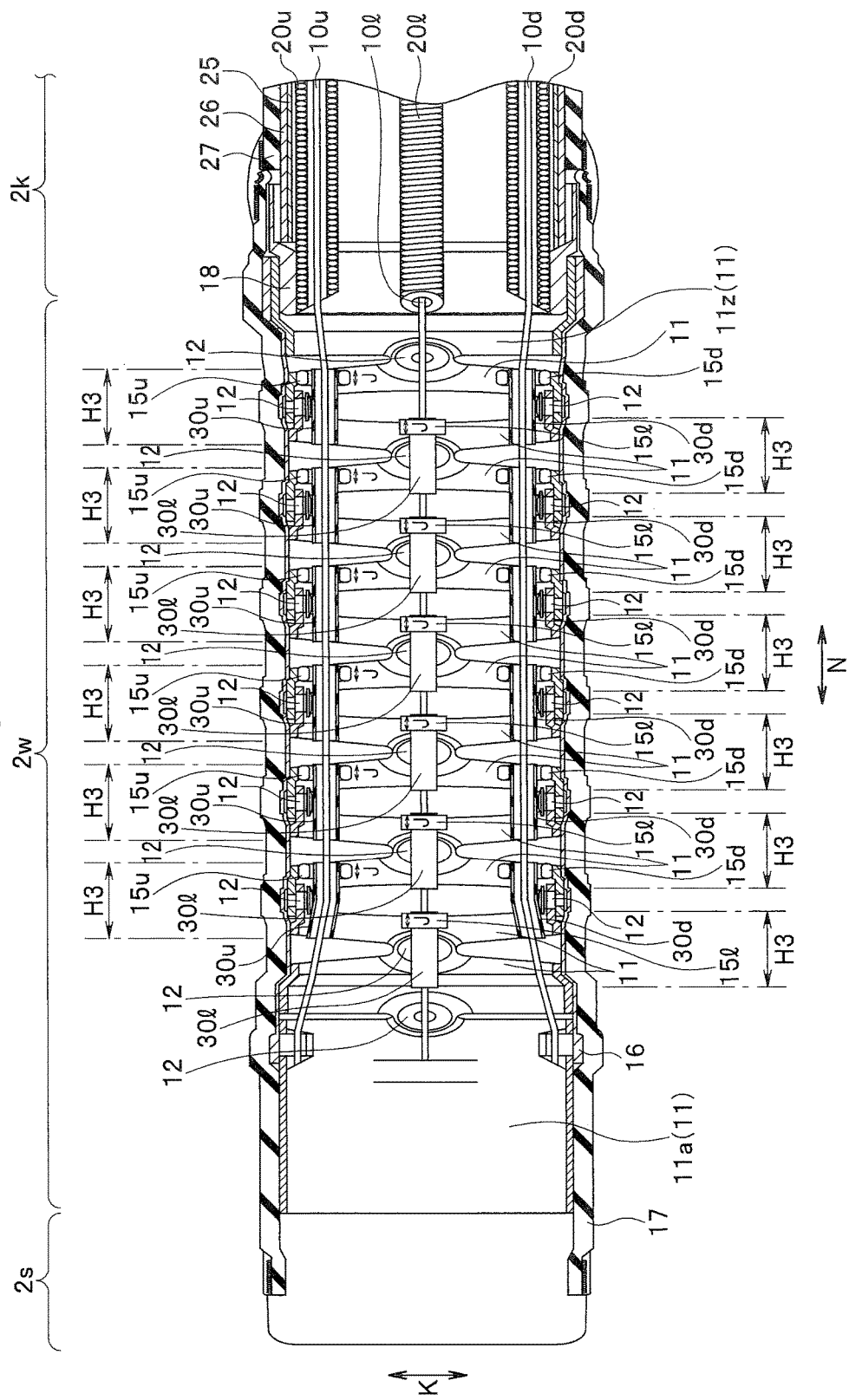
FIG. 5 is a partial sectional view of an insertion section of an endoscope including a bending device in a third embodiment.

FIG. 5 is a partial sectional view of an insertion section of an endoscope including a bending device in the present embodiment.

A configuration of the bending device in the third embodiment is different from the bending device in the first embodiment shown in FIG. 1 to FIG. 3 and the bending device in the second embodiment shown in FIG. 4 in a range in which the covers are provided in the bending section. Therefore, only the difference is described. Components same as the components in the first and second embodiments are denoted by the same reference numerals and signs and explanation of the components is omitted.

As shown in FIG. 5, in the present embodiment, the respective covers 30r to 30d (the cover 30r is not shown in the figure) are discontinuously configured in plurality from a distal end to a proximal end in the longitudinal axis direction N in the bending section 2w.

More specifically, the respective covers 30r to 30d are discontinuously covered on the outer circumferences of the respective wires 10r to 10d only in regions where the respective wire receivers 15r to 15d and the respective rivets 12 are provided while each having length H3 in the longitudinal axis direction N.

The respective covers 30r to 30d configured from the pluralities of covers are respectively fixed to the respective wire receivers 15r to 15d by soldering, brazing, or the like.

Therefore, in the present embodiment, the discontinuous respective covers 30r to 30d configured from the pluralities of covers may be configured from densely wound coils because the covers 30r to 30d are not compressed even if the bending section 2w is bent.

Note that, in the present embodiment, as in the first and second embodiments, the respective covers 30r to 30d configured from the pluralities of covers are formed in a length H for covering all the regions J held by at least the respective wire receivers 15r to 15d on the outer circumferences of the respective wires 10r to 10d in the bending section 2w and are inserted through the respective wire receivers 15r to 15d with the respective wires 10r to 10d.

Note that the respective covers 30r to 30d are desirably formed in a length in the longitudinal axis direction N for covering the respective rivets 12.

With such a configuration, when the bending section 2w is bent, since the respective covers 30r to 30d are not compressed, it is possible to tow any one of the respective wires 10r to 10d with an operation force amount smaller than the operation force amount in the first and second embodiments.

Note that the other effects are the same as the effects in the first and second embodiments.

(Fourth Embodiment)

Figure 6:
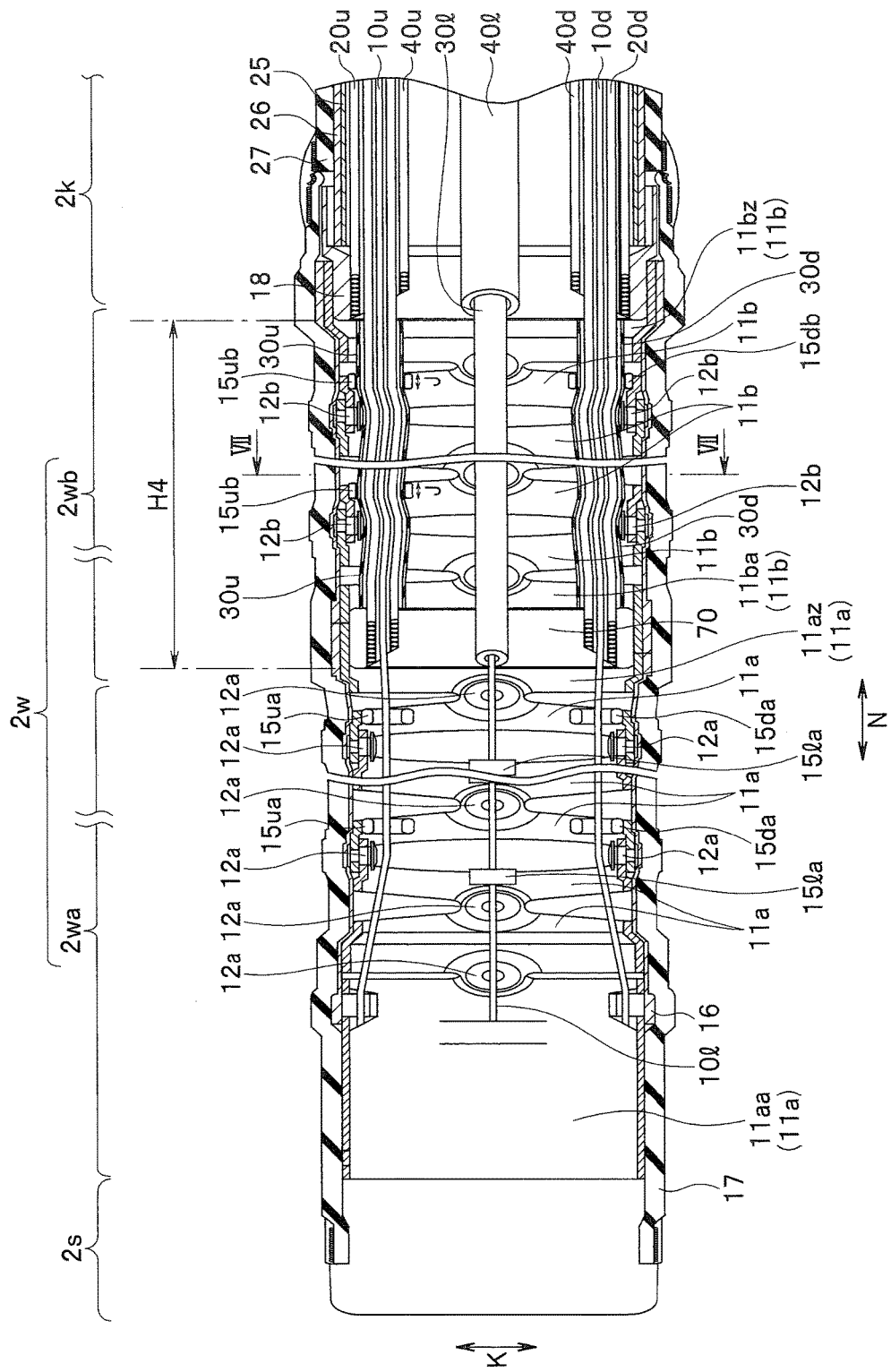
FIG. 6 is a partial sectional view of an insertion section of an endoscope including a bending device in a fourth embodiment.
Figure 7:
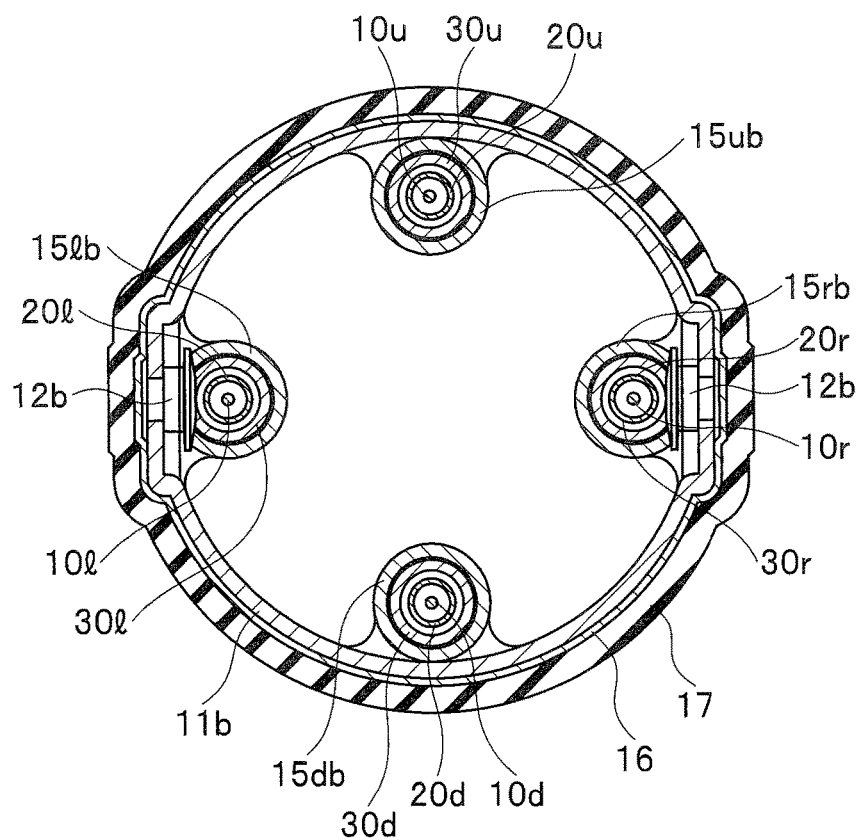
FIG. 7 is a sectional view of a second bending section taken along line VII-VIII in FIG. 6.

FIG. 6 is a partial sectional view of an insertion section of an endoscope including a bending device in the present embodiment. FIG. 7 is a sectional view of a second bending section taken along line VII-VIII in FIG. 6.

A configuration of the bending device in the fourth embodiment is different from the bending devices in the first to third embodiments shown in FIG. 1 to FIG. 5 in that a bending section of an insertion section of an endoscope in which the bending device is provided is configured from a first bending section and a second bending section and in that covers are covered on outer circumferences of inner coil sheaths in the second bending section. Therefore, only the difference is described. Components same as the components in the first to third embodiments are denoted by the same reference numerals and signs and explanation of the components is omitted.

As shown in FIG. 6, in the present embodiment, the bending section 2w is configured from a first bending section 2wa configuring the bending device and a second bending section 2wb configuring the bending device concatenated to a proximal end of the first bending section 2wa.

The first bending section 2wa is independently bendable, for example, in upward, downward, left, and right four directions by the bending operation knobs 4 and 6 provided in the operation section 3.

The second bending section 2wb is bendable, for example, in the upward, downward, left, and right four directions with the first bending section 2wa by the bending operation knobs 4 and 6 provided in the operation section 3.

In the present embodiment, in the operation section 3, a not-shown switching lever configuring a switching mechanism configured to switch fixing or unfixing of proximal ends of inner coil sheaths 20r, 20l, 20u, and 20d described below inserted through the insertion section 2 and the operation section 3 is provided.

On an inside of the first bending section 2wa, a plurality of cylindrical bending pieces 11a are coupled and provided along the longitudinal axis direction.

Note that the plurality of bending pieces 11a are turnably coupled to pieces adjacent to one another in the longitudinal axis direction N by a plurality of rivets 12a to be bendable in the upward, downward, left, and right four directions.

On an inside of the second bending section 2wb, a plurality of cylindrical bending pieces 11b are coupled and provided along the longitudinal axis direction N.

Note that the plurality of bending pieces 11b are turnably coupled to pieces adjacent to one another in the longitudinal axis direction N by a plurality of rivets 12b to be bendable in the upward, downward, left, and right four directions.

Note that the braid 16 is covered on outer circumferences of the pluralities of bending pieces 11a and 11b. The bending rubber 17 is covered on the outer circumference of the braid 16.

The first bending section 2wa and the second bending section 2wb are coupled along the longitudinal axis direction N by a connection cap 70.

More specifically, a bending piece 11az located on a most proximal end side in the first bending section 2wa and a bending piece 11ba located on a most distal end side in the second bending section 2wb are fit to an outer circumference of the connection cap 70, whereby the first bending section 2wa and the second bending section 2wb are connected via the connection cap 70.

Note that a proximal end of the first bending section 2wa and a distal end of the second bending section 2wb may be directly connected without using the connection cap 70 for the connection of the first bending section 2wa and the second bending section 2wb.

As shown in FIG. 7, the four wires 10r to 10d movable back and forth for bending the first bending section 2wa or the first bending section 2wa and the second bending section 2wb are inserted through the insertion section 2 and the operation section 3 while being shifted from one another in a circumferential direction of the insertion section 2 by approximately 90°. As shown in FIG. 6, the distal ends of the respective wires 10r to 10d are fixed to a bending piece 11aa located on a most distal end side among the plurality of bending pieces 11a provided in the first bending section 2wa.

Pluralities of tubular wire receivers 15ra, 151a, 15ua, and 15da (the wire receiver 15ra is not shown in the figure), which are bending devices that hold the wires 10r to 10d such that the respective wires 10r to 10d are located along inner circumferential surfaces of the respective bending pieces 11a and located to be shifted from one another in the circumferential direction by approximately 90°, are fixed on the inner circumferential surfaces of the respective bending pieces 11a.

Note that the wire 10r is inserted through the plurality of wire receivers 15ra having a set interval in the longitudinal axis direction N. The wire 101 is inserted through the plurality of wire receivers 151a having the set interval in the longitudinal axis direction N. Further, the wire 10u is inserted through the plurality of wire receivers 15ua having the set interval in the longitudinal axis direction N. The wire 10d is inserted through the plurality of wire receivers 15da having the set interval in the longitudinal axis direction N.

Respective proximal ends of two wires 10u and 10d for up-down bending are wound on the pulley for up-down bending described above. Respective proximal ends of two wires 10r and 10l for left-right bending are wound on the pulley for left-right bending described above.

That is, when the bending operation knob 4 is operated, one of the two wires 10u and 10d for up-down bending is moved backward and the other is moved forward by the pulley for up-down bending. That is, one is towed and the other is slacked, whereby the first bending section 2wa or the first bending section 2wa and the second bending section 2wb bend in the upward or downward direction.

When the bending operation knob 6 is operated, one of the two wires 10r and 10l for left-right bending is moved backward and the other is moved forward by the pulley for left-right bending. That is, one is towed and the other is slacked, whereby the first bending section 2wa or the first bending section 2wa and the second bending section 2wb bend in the left or right direction.

In the second bending section 2wb, a distal end side of the coupling member 18 is fixed to an inner circumference of a bending piece 11bz located on a most proximal end side among the plurality of bending pieces 11b.

As shown in FIG. 7, in the second bending section 2wb and the flexible tube 2k, inner coil sheaths 20r, 20l, 20u, and 20d configuring, for example, a flexible bending device elongated along the longitudinal axis direction N are respectively covered on the outer circumferences of the four respective wires 10r to 10d.

That is, in the operation section 3 and the insertion section 2, the four respective inner coil sheaths 20r to 20d are inserted in positions shifted from one another in the circumferential direction of the insertion section 2 by approximately 90°. Note that the respective inner coil sheaths 20r to 20d are formed for, for example, densely wound coils of stainless steel.

Note that the respective inner coil sheaths 20r to 20d are configured from the flexible densely wound coils because, for example, if normal hard pipes made of metal are covered on the outer circumferences of the respective wires 10r to 10d, the second bending section 2wb does not bend and the flexibility of the flexible tube 2k is deteriorated.

In the respective inner coil sheaths 20r to 20d, the respective wires 10r to 10d are movable back and forth.

Further, as shown in FIG. 7, in the second bending section 2wb, pluralities of tubular wire receivers 15rb, 15lb, 15ub, and 15db, which are bending devices that hold the respective inner coil sheaths 20r to 20d such that the respective inner coil sheaths 20r to 20d are located along inner circumferential surfaces of the respective bending pieces 11b and located to be shifted from one another in the circumferential direction by approximately 90°, are fixed on the inner circumferential surfaces of the respective bending pieces 11b.

That is, the respective inner coil sheaths 20r to 20d are respectively inserted through the respective wire receivers 15rb to 15db.

Note that the inner coil sheath 20r is inserted through the plurality of wire receivers 15rb having a set interval in the longitudinal axis direction N. The inner coil sheath 20l is inserted through the plurality of wire receivers 151b having the set interval in the longitudinal axis direction N. Further, the inner coil sheath 20u is inserted through the plurality of wire receivers 15ub having the set interval in the longitudinal axis direction N. The inner coil sheath 20d is inserted through the plurality of wire receivers 15db having the set interval in the longitudinal axis direction N.

Distal ends of the respective inner coil sheaths 20r to 20d are respectively fixed to a distal end of the second bending section 2, more specifically, the connection cap 70 by, for example, brazing.

Note that respective proximal ends of the respective inner coil sheathes 20r to 20d are configured such that a fixed state and an unfixed state can be switched by the switching mechanism described above provided in the operation section 3.

Further, outer coil sheathes 40r, 40l, 40u, and 40d (the outer coil sheathes 40r is not shown in the figure) configured from, for example, flexible coil pipes are respectively covered on outer circumferences of the four inner coil sheathes 20r to 20d located in the flexible tube 2k.

Note that the respective inner coil sheathes 20r to 20d inserted through the respective outer coil sheathes 40r to 40d are advanceable and retractable to the front and the back in the longitudinal axis direction N. The respective outer coil sheathes 40r to 40d are formed of, for example, densely wound coils of stainless steel.

Distal ends of the respective outer coil sheathes 40r to 40d are fixed to the distal end of the flexible tube 2k, more specifically, the coupling member 18 by, for example, brazing. Proximal ends of the respective outer coil sheathes 40r to 40d are fixed to a not-shown stopping member by, for example, brazing in the proximal end of the flexible tube 2k or in the operation section 3.

In this way, the respective outer coil sheathes 40r to 40d are inserted through the flexible tube 2k in a state in which the distal ends and the proximal ends are fixed. Consequently, when any one of the four wires 10r to 10d is towed to bend the first bending section 2wa or the first bending section 2wa and the second bending section 2wb, the respective outer coil sheathes 40r to 40d resist a compression force acting on the flexible tube 2k along the longitudinal axis direction N of the outer coil sheathes 40r to 40d.

Consequently, it is possible to prevent even the flexible tube 2k having flexibility from bending with the first bending section 2wa or the first bending section 2wa and the second bending section 2wb.

Therefore, in such a configuration, first, when desiring to bend the first bending section 2wa and the second bending section 2wb, an operator releases the fixing of the proximal ends of the respective inner coil sheathes 20r to 20d without performing operation of the switching lever.

In this state, when the operator operates one of the bending operation knobs 4 and 6 to tow any one of the four wires 10r to 10d, for example, the wire 10l, since the proximal ends of the respective inner coil sheathes 20r, 20u, and 20d are not fixed, the respective inner coil sheathes 20r, 20u, and 20d cannot resist a compression force acting along the longitudinal axis direction N of the respective inner coil sheathes 20r, 20u, and 20d in the second bending section 2wb. The respective proximal ends move backward.

In the flexible tube 2k, since the distal ends and the proximal ends of the respective outer coil sheathes 40r to 40d are fixed, the respective outer coil sheathes 40r to 40d resist the compression force acting along the longitudinal axis direction N of the respective outer coil sheathes 40r to 40d.

As a result, the first bending section 2wa and the second bending section 2wb bend in the left direction. Note that the same applies when the first bending section 2wa and the second bending section 2wb are bent in any one of the right direction, the upward direction, and the downward direction.

When desiring to bend only the first bending section 2wa, the operator performs operation of the switching lever of the operation section 3 and fixes, with the switching mechanism, the proximal ends of the respective inner coil sheathes 20r to 20d.

In this state, when the operator operates one of the bending operation knobs 4 and 6 to tow any one of the four wires 10r to 10d, for example, the wire 10l, since the proximal ends are fixed, the respective inner coil sheathes 20r to 20d resist a compression force acting along the longitudinal axis direction N of the respective inner coil sheathes 20r to 20d in the second bending section 2wb.

As a result, only the first bending section 2wa bends in the left direction. Note that the same applies when only the first bending section 2wa is bent in any one of the right direction, the upward direction, and the downward direction.

As shown in FIG. 6 and FIG. 7, in the second bending section 2wb, the respective covers 30r to 30d are covered on outer circumferences of the respective inner coil sheathes 20r to 20d from the distal end to the proximal end of the second bending section 2wb in the longitudinal axis direction N while having length H4.

That is, in the second bending section 2wb, the respective covers 30r to 30d are inserted through the respective wire receivers 15r to 15d with the respective inner coil sheathes 20r to 20d and the respective wires 10r to 10d.

Note that, in the second bending section 2wb, the respective covers 30r to 30d are advanceable and retractable according to compression involved in the bending of the second bending section 2wb. The distal ends of the respective covers 30r to 30d are butted against fixed sections at the distal ends of the respective inner coil sheathes 20r to 20d with respect to the connection cap 70. The proximal ends of the respective covers 30r to 30d are abutted against the distal ends of the respective outer coil sheathes 40r to 40d.

Note that, in the present embodiment, in the second bending section 2wb, the respective covers 30r to 30d are covered on all the regions J held by at least the respective wire receivers 15rb to 15db in the outer circumferences of the respective wires 10r to 10d and the respective inner coil sheathes 20r to 20d.

The respective covers 30r to 30d, regardless of the covers advancing/retracting after compression with respect to the respective wire receivers 15rb to 15db in the longitudinal axis direction N of the covers 30r to 30d involved in the bending of the second bending section 2wb, are formed in the length H4 in the longitudinal axis direction N for covering all the regions J held by the respective wire receivers 15rb to 15db.

Note that the respective covers 30r to 30d, regardless of the covers advancing/retracting after compression with respect to the respective rivets 12 in the longitudinal axis direction N of the respective covers 30r to 30d involved in the bending of the second bending section 2wb, are preferably formed in a length in the longitudinal axis direction N for covering the respective rivets 12.

With such a configuration, when the second bending section 2wb is bent with the first bending section 2wa, in the second bending section 2wb, the respective inner coil sheathes 20r to 20d are prevented from locally coming into contact with the respective wire receivers 15rb to 15db by the respective covers 30r to 30d. Therefore, an operation force amount of the respective wires 10r to 10d does not increase.

When the second bending section 2wb is bent, the respective inner coil sheathes 20r to 20d advance and retract with the respective wires 10r to 10d. Therefore, it is possible to bend the second bending section 2wb in an intended shape.

Note that the other effects are the same as the effects in the first to third embodiments described above.

Consequently, it is possible to provide the bending device including a configuration for preventing, when the second bending section 2wb is bent with the first bending section 2wa by towing of the respective wires 10r to 10d, an operation force amount of the respective wires 10r to 10d from increasing while securing durability of the respective inner coil sheathes 20r to 20d.

In the first to fourth embodiments described above, the bending device provided in the endoscope 1 is described as an example. However, the present invention is not limited to this. It goes without saying that the present invention is also applicable to a treatment instrument including coil sheathes and wires in a flexible tube and a grasping section operates according to towing of the wires, for example, a manipulator insertable into a channel of an endoscope.

What is claimed is:

1. A bending device comprising:
   a bendable bending section in which a plurality of bending pieces are coupled;
   a wire, a distal end of the wire being fixed to the bending section, the wire being towed to bend the bending section;
   a plurality of wire receivers provided on an inner circumferential surface of the bending section, the wire being inserted through the wire receivers in an advanceable and retractable manner;
   an inner coil sheath, a distal end of the inner coil sheath being fixed to a cap, the cap being interposed between the bending pieces in an intermediate section of the bending section, the inner coil sheath being inserted through the plurality of wire receivers that are closer to a proximal end of the bending section than the cap and the inner coil sheath extending toward the proximal end of the bending section;
   an outer coil sheath, the inner coil sheath being inserted through the outer coil sheath, the outer coil sheath being arranged proximally relative to the cap;
   a cover that covers an entirety of a region of the inner coil sheath inserted through the plurality of wire receivers on an outer circumference of the inner coil sheath between the cap and the outer coil sheath in a longitudinal axis direction of the wire, the cover being inserted through the wire receivers with the wire, the cover having stretchability in the longitudinal axis direction of the wire, and the cover being advanceable and retractable in the longitudinal axis direction in the bending section between the cap and the outer coil sheath;
   wherein a distal end of the cover abuts a proximal end portion of the cap when the cover advances and retracts in the bending section; and
   a proximal end of the cover abuts a distal end portion of the outer coil sheath when the cover advances and retracts in the bending section.

2. The bending device according to claim 1, wherein the cover is configured from a sparsely wound coil.

3. The bending device according to claim 1, wherein the cover has a constant stretching ratio over an entire length in the longitudinal axis direction.

4. The bending device according to claim 1, wherein the cover is formed, regardless of the covers advancing/retracting with respect to the wire receiver in the longitudinal axis direction of the cover involved in the bending of the bending section, in a length in the longitudinal axis direction for covering the entirety of the region.

5. The bending device according to claim 1, wherein the cover is covered on the outer circumference of the wire such that the distal end of the cover is located to be proximally separated in the longitudinal axis direction by a set interval relative to the distal end of the wire.

6. The bending device according to claim 1, wherein
   the bending section is configured from a first bending section that is concatenated to a distal end side of the cap and independently bends according to the towing of the wire and a second bending section that is concatenated to a proximal end side of the cap and bends with the first bending section according to the towing of the wire,
   the distal end of the wire is fixed to a distal end in the longitudinal axis direction of the first bending section,
   a proximal end in the longitudinal axis direction of the inner coil sheath is configured such that a fixed state and an unfixed state can be switched,
   when the proximal end of the inner coil sheath is in the fixed state, only the first bending section bends according to the towing of the wire and, when the proximal end of the inner coil sheath is in the unfixed state, the first bending section and the second bending section bend according to the towing of the wire, and
   the cover is covered on an outer circumference of the inner coil sheath in the second bending section.

7. An endoscope comprising the bending device according to claim 1.

* * * * *